US006375612B1

(12) United States Patent
Guichon et al.

(10) Patent No.: US 6,375,612 B1
(45) Date of Patent: *Apr. 23, 2002

(54) METHOD AND SYSTEM FOR MONITORING ANIMALS

(76) Inventors: P. Timothy Guichon; G. Kee Jim, both of Postal Bag 5, Bay 8 87 Elizabeth Street, Okotoks, Alberta (CA), T0L 1T0; P. Bernard Kotelko; Michael J. Kotelko, both of Box 57, Vegreville, Alberta (CA), T9C 1R1; Calvin W. Booker, Postal Bag 5, Bay 8 87 Elizabeth Street, Okotoks, Alberta (CA), T0L 1T0; Yvonne T. G. Tollens, 47-1011 Canterbury Dr. S.W., Calgary, Alberta (CA), T2W 2S8

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/047,088

(22) Filed: Mar. 24, 1998

(51) Int. Cl.[7] ................................................. A61B 5/00
(52) U.S. Cl. ..................... 600/300; 119/51.02; 128/903; 705/2
(58) Field of Search ................................. 600/300–301, 600/529–538, 595; 119/51.02, 842, 455; 128/903, 904, 920–925; 705/2–4

(56) References Cited

U.S. PATENT DOCUMENTS

| | | |
|---|---|---|
| 4,448,150 A | 5/1984 | Catsimpoolas |
| 4,618,861 A | 10/1986 | Gettens et al. |
| 4,917,117 A | 4/1990 | Brom et al. |
| 5,069,165 A | 12/1991 | Rousseau |
| 5,315,505 A | 5/1994 | Pratt et al. |
| 5,461,365 A | 10/1995 | Schlager et al. |
| 5,474,085 A | 12/1995 | Harnik et al. |
| 5,559,520 A | 9/1996 | Barzegar et al. |
| 5,650,770 A | 7/1997 | Schlager et al. |
| 5,663,734 A | 9/1997 | Krasner |
| 5,673,647 A | 10/1997 | Pratt |
| 5,867,820 A | * 2/1999 | Cureton et al. ................. 705/1 |
| 6,000,361 A | * 12/1999 | Pratt ....................... 119/51.02 |
| 6,032,084 A | * 2/2000 | Anderson et al. ........... 700/241 |

FOREIGN PATENT DOCUMENTS

| | | |
|---|---|---|
| CA | 1311057 | 4/1989 |
| CA | 1296068 | 2/1992 |
| DE | 297 02 444 U 1 | 5/1997 |
| EP | 0 624 313 A1 | 11/1994 |
| EP | 0 808 567 A1 | 11/1997 |
| GB | 2270405 | 3/1994 |
| WO | WO 97/24027 | 12/1996 |
| WO | WO 97/00708 | 1/1997 |

OTHER PUBLICATIONS

Arthur R. Rodger, Ph.D., Centre for Northern Forest Ecosystem Research, Ontario Ministry of Natural Resources, Moose Guidelines Evaluation Program (Oct. 15, 1997) http://www.cnfer.on.ca/moose-guide.htm.

B.F. Sowell, J.G.P. Bowman, C. Huisma, M.E. Branine, M.E. Hubbert, "Feeding Behavior of Feedlot Cattle," pp. 45–49.

Christine McClintic, Rollie Henkes, "Electronic Branding for Livestock".

* cited by examiner

Primary Examiner—John P. Lacyk
Assistant Examiner—Michael Astorino
(74) Attorney, Agent, or Firm—Piper Marbury Rudnick & Wolfe; Jefferson Perkins

(57) ABSTRACT

In a method of monitoring animals within an area, position data of each animal within the area is collected at interval. The position data is then processed to generate movement pattern data of the animals. The movement pattern data is then analyzed to determine at least one physical condition of the animals.

31 Claims, 11 Drawing Sheets

| ANIMAL HEALTH | |
|---|---|
| ANIMAL | DAYS ON FEED |
| A | 40 |
| B | 65 |
| C | 135 |
| D | 10 |
| • | • |
| • | • |
| • | • |

| ZONE DEFINITION | |
|---|---|
| FEEDLOT PEN A | |
| ZONE | XY COORDINATES |
| 14 | (DATA SET) |
| 16 | (DATA SET) |
| 18 | (DATA SET) |
| 20 | (DATA SET) |
| • | • |
| • | • |
| • | • |

PHYSICAL CONDITION TABLE

| | | |
|---|---|---|
| ANIMAL HEALTH | | |
| | RESPIRATORY DISORDER | REFERENCE MOVEMENT PATTERN DATA 1 |
| | GASTROINTESTINAL DISORDER | REFERENCE MOVEMENT PATTERN DATA 2 |
| | ⋮ | ⋮ |
| PERFORMANCE CHARACTERISTICS | | |
| | YIELD GRADE 1 | REFERENCE MOVEMENT PATTERN DATA 10 |
| | YIELD GRADE 2 | REFERENCE MOVEMENT PATTERN DATA 11 |
| | ⋮ | ⋮ |
| | QUALITY GRADE PRIME | REFERENCE MOVEMENT PATTERN DATA 15 |
| | ⋮ | ⋮ |
| PRODUCTION CHARACTERISTICS | | |
| | MARKET READY | REFERENCE MOVEMENT PATTERN DATA 20 |
| | ⋮ | ⋮ |

FIG. 5A-2

| | |
|---|---|
| REFERENCE MOVEMENT PATTERN DATA 1 | FREQUENCY WATER ZONE (HIGH) ≥ A<br>DURATION WATER ZONE (HIGH) ≥ B<br>FREQUENCY FOOD ZONE (LOW) ≤ C<br>DURATION FOOD ZONE (LOW) ≤ D<br>OVERALL ACTIVITY (LOW) ≤ E |
| REFERENCE MOVEMENT PATTERN DATA 2 | FREQUENCY WATER ZONE (HIGH) ≥ A<br>DURATION WATER ZONE (LOW) ≥ B<br>FREQUENCY FOOD ZONE (LOW) ≤ C<br>DURATION FOOD ZONE (LOW) ≤ D |
| ⋮ | ⋮ |
| REFERENCE MOVEMENT PATTERN DATA 10 | FREQUENCY FOOD ZONE (HIGH) ≥ A<br>DURATION FOOD ZONE (HIGH) ≥ B<br>DAYS ON FEED ≥ F |
| ⋮ | ⋮ |
| REFERENCE MOVEMENT PATTERN DATA 20 | FREQUENCY FOOD ZONE (MED) ≤ A<br>FREQUENCY FOOD ZONE (MED) ≥ C<br>DURATION FOOD ZONE (MED) ≤ B<br>DURATION FOOD ZONE (MED) ≥ D<br>DAYS ON FEED ≥ G |

FIG. 5B

| TAG NUMBER | X | Y | TIME | ZONE IN | ZONE FROM |
|---|---|---|---|---|---|
| A | $X_1$ | $Y_1$ | 11:01 | 14 | 20 |
| A | $X_2$ | $Y_2$ | 11:15 | 14 | 14 |
| A | $X_3$ | $Y_3$ | 11:25 | 14 | 14 |
| A | $X_4$ | $Y_4$ | 11:35 | 14 | 14 |
| A | $X_5$ | $Y_5$ | 11:45 | 16 | 14 |
| . | . | . | . | . | . |
| . | . | . | . | . | . |
| . | . | . | . | . | . |

FIG. 5C

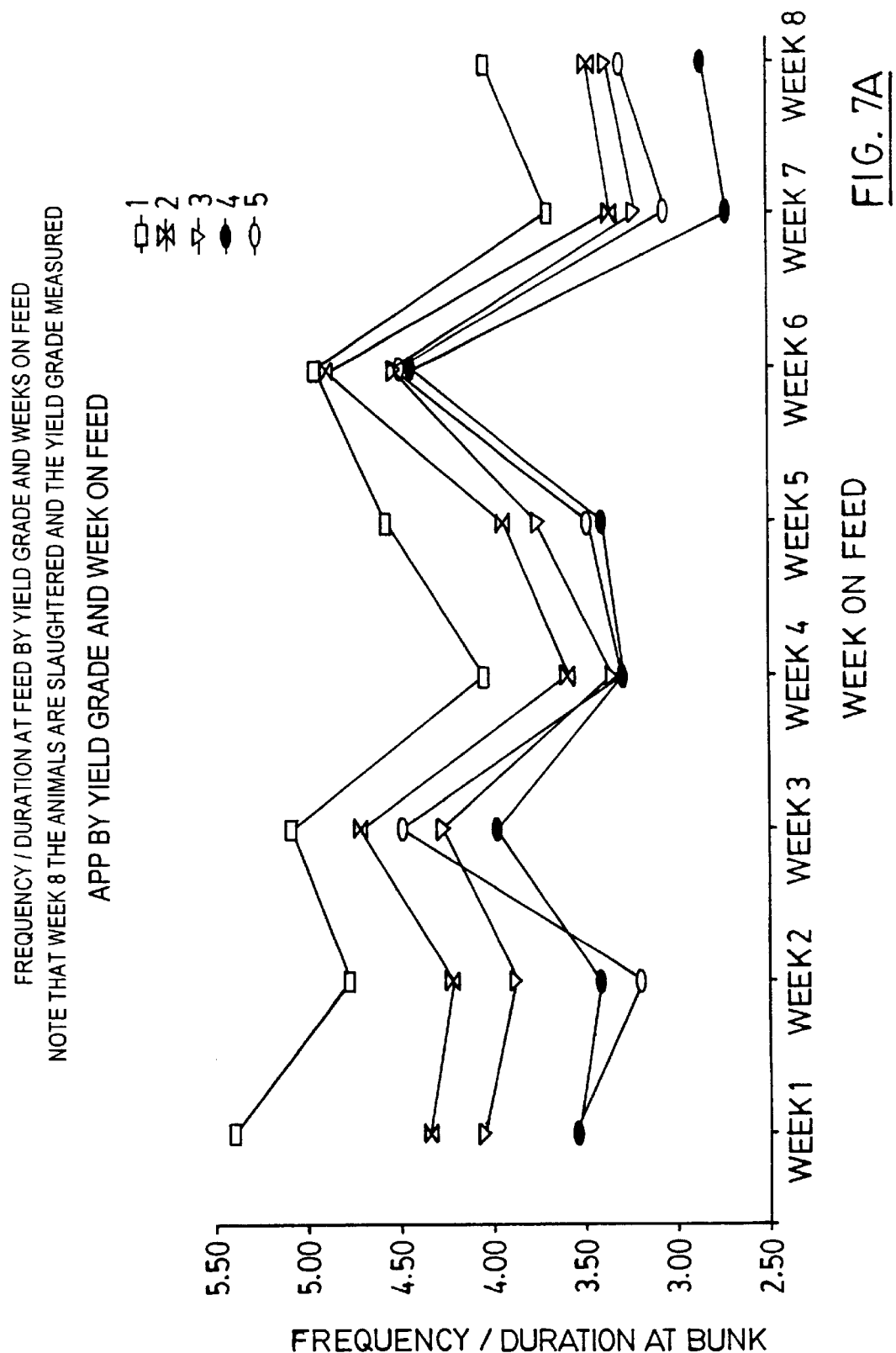

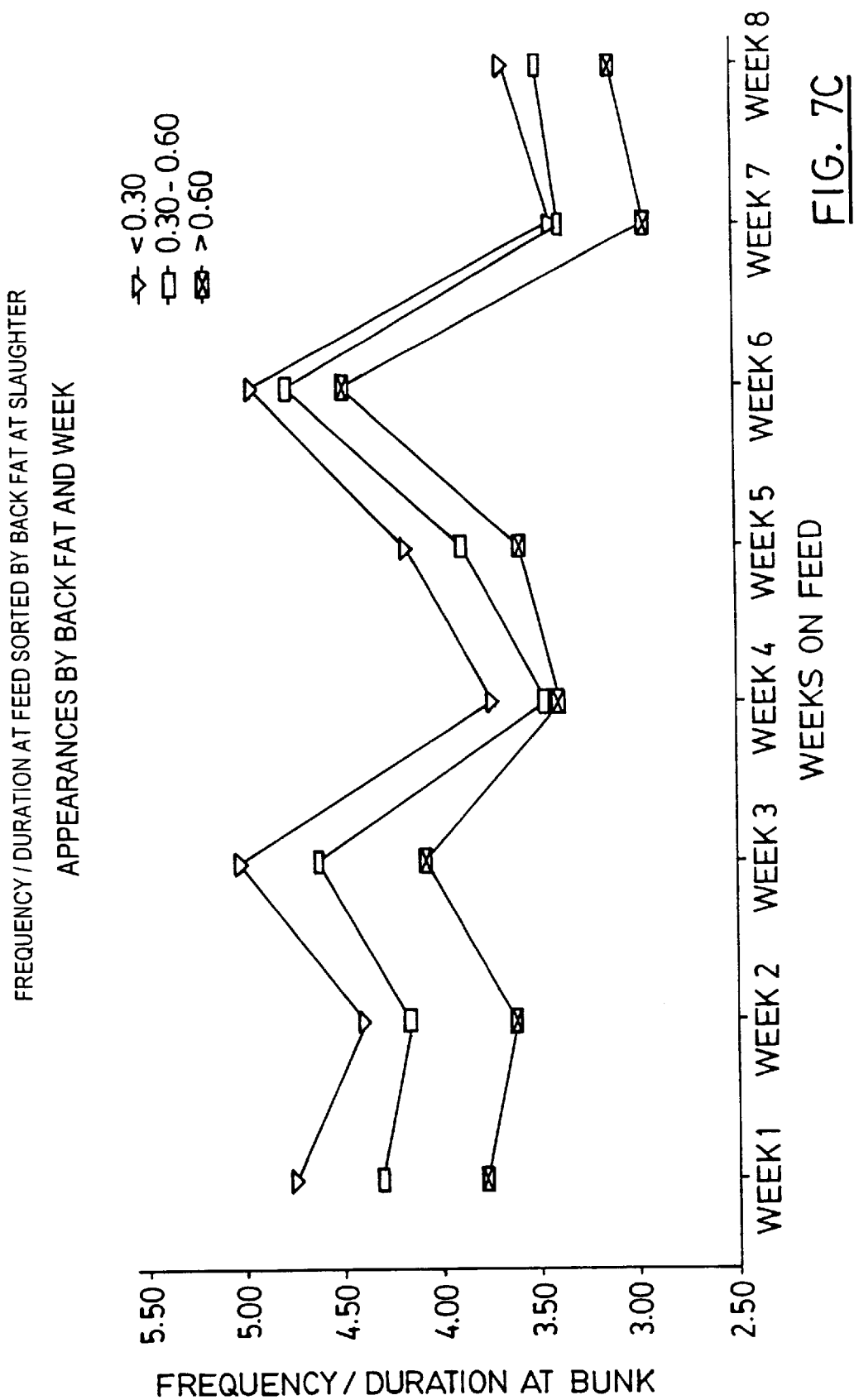

METHOD AND SYSTEM FOR MONITORING ANIMALS

FIELD OF THE INVENTION

The present invention relates to tracking systems and in particular to a system and method for monitoring the movement of animals within an area to determine at least one physical condition of the animals.

BACKGROUND OF THE INVENTION

During the preparation of livestock for slaughter, the livestock are brought to a feedlot. At the feedlot, the livestock are processed in a hospital and processing area and treated with a variety of drugs before being delivered to pens in the feedlot. In the feedlot pens, the animals' rations are varied at specific times to prepare the animals for slaughter. During the animals' stay in the feedlot, the animals are examined regularly by sight to detect sick animals as well as animals which appear ready for market. This requires individuals to move through the feedlot pens on horseback resulting in the livestock being disrupted and their stress levels increased.

When an animal is determined to be market ready, the animal is shipped to the slaughterhouse. At the slaughterhouse, the quality of the animal is evaluated based on one of two government standards, namely yield grade or quality grade. Yield grade is a measure of an animal's red meat to fat and bone ratio. Yield grade 1, the most attractive, has a high red meat to fat and bone ratio while yield grade 5, the least attractive, has a low red meat to fat and bone ratio. Quality grade is a measure of an animal's intramuscular fat associated with quality. In the United States, the four quality grades are Prime, Choice, Select and Standard. In Canada, the four corresponding quality grades are Prime, AAA, AA and A.

Ideally, animals that are shipped to the slaughterhouse meet high quality standards since penalties are imposed on the feedlot operator for animals that do not meet quality standards. The tendency therefore, is for feedlot operators to put animals on feed for longer durations even though the animals may be considered market ready. This poses problems in that feed costs and methane or greenhouse gas production are increased.

When an animal is identified as being "sick", the animal is physically captured and taken to a hospital where the animal's temperature is taken to determine if in fact the animal is sick. Physically capturing the animal of course causes significant stress. If the animal is sick, the animal is treated with a range of antibiotics to cure many illnesses regardless of whether the animal requires treatment for all of these illnesses. If the animal is not sick, the animal is returned to the feedlot after having been stressed for no reason. Unfortunately, visual inspection of livestock to determine sickness is subjective making the accuracy of this method questionable. Also, significant lengths of time may elapse before sick animals are in fact visually identified as being sick. As will be appreciated, this prior art method of monitoring livestock in a feedlot suffers many disadvantages.

Systems to monitor animals remotely to collect data concerning the condition of the animals are known. For example, U.S. Pat. No. 5,474,085 to Hurnik et al. discloses an apparatus for remote sensing of livestock using a thermographic imaging system. The thermographic imaging system remotely monitors the location, weight and temperature of livestock by taking thermographic images of the animals. The thermographic images are digitized and converted into number arrays. The number arrays are interpreted by software executed by a computer to provide weight information in a decipherable form concerning the animals.

Canadian Patent No. 1,296,068 to Friesen discloses a physiological monitoring system to measure physiological functions such as the pulse rate or temperature of an animal. The system includes a remote telemetry system carried by the animal including sensors to sense conditions of the animal and store data representing the sensed conditions. The stored data is then transmitted to a master telemetry system for processing.

In the article entitled "Feeding Behavior of Feedlot Cattle" authored by Sowell et al., a system to measure the feeding behavior of feedlot cattle by monitoring cattle at a feedbunk is described. The system includes passive radio frequency (RF) tags carried by the cattle. A read panel in close proximity to the feedbunk communicates with the RF tags carried by cattle at the feedbunk to allow the presence and location of the cattle at the feedbunk to be recorded. The recorded information is processed to determine the average time untreated and treated cattle spend at the feedbunk.

Although the above-identified references disclose systems to monitor animals remotely, improved systems to provide information concerning the physical condition of animals within an area are desired.

It is therefore an object of the present invention to provide a novel method and system for monitoring animals within an area to determine at least one physical condition of the animals.

SUMMARY OF THE INVENTION

According to one aspect of the present invention there is provided a method of monitoring the movement of animals within an area comprising the steps of:

collecting positional data of each animal under observation;

processing said positional data to generate data representing the movement patterns of said animals; and analyzing said movement pattern data to determine at least one physical condition of said animals.

In a preferred embodiment, the positional data is collected remotely and at intervals. During the analyzing step, the movement pattern data is compared with reference movement pattern data stored in a database representing typical movement patterns of animals exhibiting the at least one physical condition. The movement pattern data is compared with the reference movement pattern data to detect animals suspected of suffering a health problem. In this regard it is preferred that the movement pattern data is compared with the reference movement pattern data to detect animals exhibiting one or more of the following characteristics:

more frequent and longer duration visits to the water zone;

less frequent visits to the water zone;

generally overall decreased movement within the area;

more frequent and shorter duration visits to the water zone; and less frequent and shorter duration visits to the water zone.

It is also preferred that the movement pattern data is compared with reference movement pattern data to detect the frequency and duration animals spend in the food zone either to determine a yield or quality grade for each animal. Furthermore, it is preferred that the movement pattern data is compared with reference movement pattern data to determine market ready animals. In this case, market ready animals can be shipped to slaughterhouses more quickly and reductions in greenhouse gas production can be calculated and sold as offsets to greenhouse gas producers.

According to another aspect of the present invention there is provided a system for monitoring the movement of animals within an area comprising:

a plurality of data collection and transmission units, each being carried by a respective animal, each of said data collection and transmission units transmitting animal position data over a wireless communications link; and a processor in communication with said data collection and transmission units via said wireless communication link and receiving said animal position data, said processor processing said animal position data to generate data representing movement patterns of said animals and analyzing said movement pattern data to determine at least one physical condition of said animal.

According to another aspect of the present invention there is provided a system for detecting animals exhibiting at least one physical condition of interest within a predefined area comprising:

a receiver receiving position data for each of said animals under observation at intervals over a wireless communications link; and a processor in communication with said receiver and processing said position data to generate a first database including data representing the movement pattern of each of said animals within said predefined area; and a second database storing reference movement pattern data representing typical movement patterns of animals having physical conditions of interest, wherein said processor compares said movement pattern data in said first database with said reference movement pattern data in said second database to determine animals exhibiting one or more physical conditions of interest.

According to another aspect of the present invention there is provided a program product comprising:

a computer-readable storage medium:

means recorded on the medium for processing animal position data to generate data representing the movement patterns of animals; and means recorded on the medium to compare the movement pattern data with reference movement pattern data to determine at least one physical condition of said animals.

The present invention provides advantages in that by tracking the movement of each animal within the area, sick animals can be identified and treated quickly. Not only can sick animals be identified but based on their movement patterns, the cause of sickness can be better diagnosed reducing the overall amounts of antibiotics used to treat sick animals.

In the case of animals within a feedlot, the yield or quality grade of the animals can be determined during their stay at the feedlot allowing animals to be grouped according to grade and their feed composition and rations adjusted accordingly to increase performance. In addition, by tracking the movement pattern of each animal, changes in the feeding patterns of the animals can also be detected allowing market ready animals to be determined quickly. This allows feedlot operators to ship animals to the slaughterhouse faster without compromising performance resulting in reduced feed costs, a reduction in the production of greenhouse gasses by the animals and fewer animals gaining too much fat and weight. Furthermore, by monitoring the movement patterns of the animals, overfeeding and underfeeding conditions in the feedlot can also be determined allowing the feedlot operator to take appropriate action.

In other environments such as pastures and grazing pens, by monitoring the movement patterns of the animals, low food levels, poor water quality and heavy grazed areas can be determined. Also, animals in heat and those likely suffering a reproductive disorder can be determined. This allows corrective measures to be taken to improve the condition of the animals.

BRIEF DESCRIPTION OF THE DRAWINGS

Embodiments of the present invention will now be described more fully with reference to the accompanying drawings in which:

FIG. 4 is a flowchart illustrating data processing in the system for feedlot management of FIG. 2;

FIGS. 5a and 5b illustrate tables used in the system for feedlot management of FIG. 2;

FIG. 5c illustrates a virtual table created by the system for feedlot management during processing of data;

FIGS. 7a to 7d are graphs illustrating the frequency/duration of animals feeding vs. a number of different characteristics of interest.

DETAILED DESCRIPTION OF THE PREFERRED EMBODIMENTS

In general, the present invention relates to a system and method for monitoring the movement of animals within an area to determine at least one physical condition of the animals. The present inventors have found that the movement patterns of animals provide a wealth of information concerning their physical conditions including but not limited to animal health; performance characteristics such as yield grade, quality grade, back fat percentage, weight etc.; and production patterns such as market readiness, insufficient feeding, overfeeding, greenhouse gas emissions etc. During monitoring of the animals, data concerning the movement of each animal within a defined area is collected at intervals, processed and stored. Physical condition definitions including reference movement pattern data representing typical movement patterns of animals having specific characteristics, traits, behaviors, and/or conditions etc. (hereinafter collectively referred to as "conditions") of interest, are also stored. The collected animal movement data is compared with the reference movement pattern data to allow animals to be classified according to these specific conditions of interest. This allows unhealthy animals to be detected quickly and treated and animals exhibiting other specific conditions of interest to be grouped. A preferred embodiment of the present invention will now be described more fully wherein the system and method are used to monitor the movement of animals, such as cattle, in a feedlot.

Figure 1:
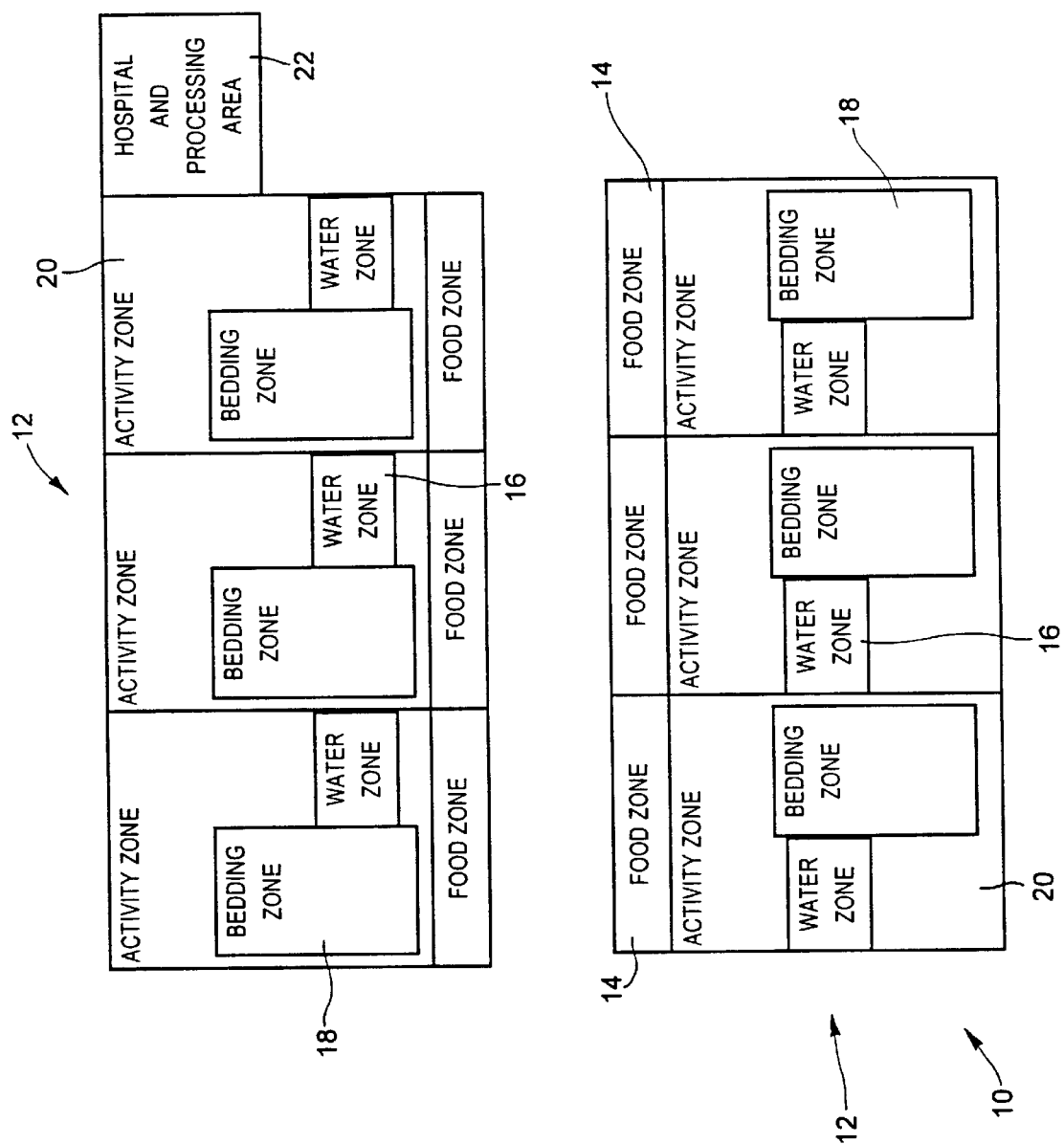
FIG. 1 is a diagram of a feedlot including a plurality of feedlot pens divided into a plurality of zones.

Referring now to FIG. 1, a feedlot is shown and is generally indicated to by reference numeral 10. As can be seen, the feedlot 10 includes a plurality of feedlot pens 12, each of which accommodates a plurality of animals (not shown). Each feedlot pen 12 is divided into a number of zones, namely a food zone 14, a water zone 16, a bedding zone 18 and an activity zone 20. Animals are free to move in the feedlot pens 12 between the various zones 14 to 20. A hospital and processing area 22 is also provided to treat sick animals removed from the feedlot pens 12 and to treat new animals entering the feedlot 10. In the present feedlot 10, the movement of each animal in its respective feedlot pen 12 is monitored and corresponding data is collected at intervals, processed and stored. In this manner, the number of times and duration each animal visits the various zones 14 to 20 within its feedlot pen 12 can be determined.

Figure 2:
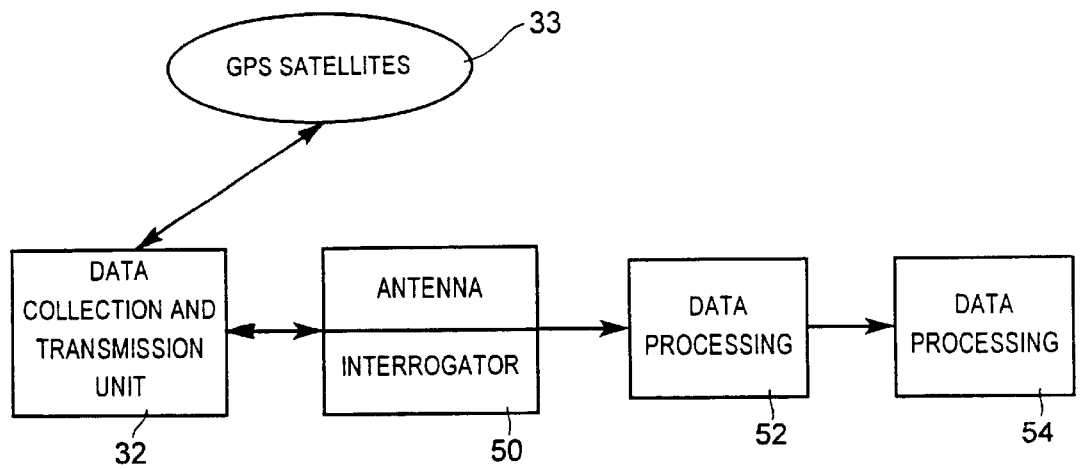
FIG. 2 is a block diagram of a system for feedlot management in accordance with the present invention.
Figure 3:
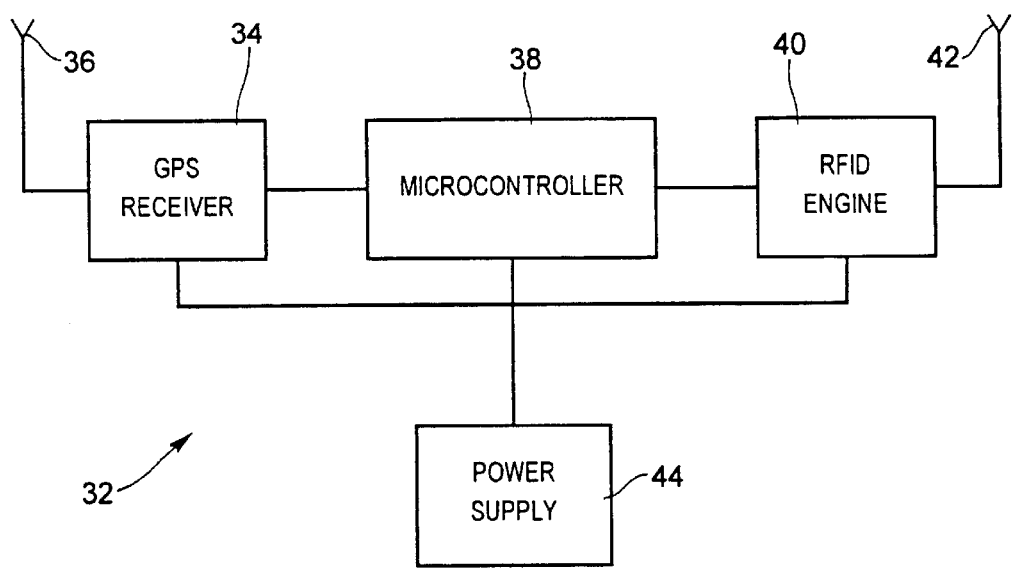
FIG. 3 is a block diagram of a data collection and transmission unit forming part of the system for feedlot management of FIG. 2.

In order to monitor the movement of the animals in each feedlot pen 12, each animal is fitted with a collar or tag (not shown) to which a data collection and transmission unit 32 is attached (see FIGS. 2 and 3). The data collection and transmission unit 32 on the tag fitted to each animal is unique to that animal and stays with the animal during its entire stay in the feedlot 10. The data collection and transmission units 32 collect raw GPS data representing their positions from orbiting GPS satellites 33. The raw GPS data is accurate to about 100 m.

Turning now to FIG. 3, one of the data collection and transmission units 32 is better illustrated. As can be seen, the data collection and transmission unit 32 includes a global positioning system (GPS) receiver 34 connected to an external antenna 36 and to a microcontroller 38 having resident memory. The microcontroller 38 is also connected to a radio frequency spread spectrum (RFID) engine 40 having an antenna 42. A power supply 44 is connected to the GPS receiver 34, microcontroller 38 and RFID engine 40.

Communicating with data collection and transmission units 32 on animal tags carried by animals in a plurality of feedlot pens 12, at user selected intervals, is an interrogator 50. The interrogator 50 also communicates with a data collection and transmission unit at a fixed location (not shown) to provide a field reference allowing GPS satellite signal propagation errors to be determined. A first processor 52 in the form of a Pentium® personal computer (PC) is connected to the interrogator 50. The processor 52 receives the raw GPS data from the interrogator 50 and processes the raw GPS data to sub-metre accuracy. Thereafter the processor 52 converts the GPS data into XY coordinates and stores the XY coordinates in an animal observation table together with other relevant information as will be described.

A second processor 54, also in the form of a personal computer, is connected to the processor 52 via a local area or wide area network. The processor 54 receives the animal observation table from processor 52 at intervals. The processor 54 executes software to process the data in the animal observation table to allow animals to be classified according to specific conditions of interest as will be described. Although not shown, the processor 54 includes a graphical user interface (GUI) to allow the results of the classifications to be visually presented and manipulated as desired.

Stored within the processor 54 are a plurality of tables (best seen in FIG. 5a), namely a zone definition table, an animal health table and a physical condition table. The zone definition table includes data defining the zones of each feedlot pen 12 in XY coordinates. The data in the zone definition table can be edited as desired allowing the zones in the feedlot pens 12 to be reconfigured. The animal health table includes data indicating the number of days each animal has been on feed since the arrival of the animal at the feedlot 10. The physical condition table stores a plurality of definitions. Each definition includes reference movement pattern data representing the typical movement pattern of an animal exhibiting a specific physical condition of interest to which the animals under observation are to be compared. The physical condition table can be edited to add or remove definitions. Also, the reference movement pattern data for each definition can be edited to update the definitions when new data becomes available.

In the present embodiment, the physical condition definitions relate to animal health, performance characteristics, and production patterns including greenhouse gas emissions. The physical condition definitions relating to animal health include reference movement pattern data modeling the typical movement patterns of animals suffering respiratory, gastrointestinal and neurological as well as muscular skeletal injuries.

The physical condition definitions relating to performance characteristics include reference movement pattern data modeling the typical movement patterns of animals of different yield grades, different quality grades, different back fat percentages, and different weights as a function of days on feed.

The physical condition definitions relating to production patterns include reference movement pattern data modeling the typical movement patterns of animals that are market ready, overfed and underfed. The definitions in the physical condition table will now be described more fully.

Animal Health

Referring now to Table 2, the typical movement patterns of animals suffering from different health problems are set out. It has been determined that animals spending more time at the water zone and visiting the water zone more often while spending less time in the food zone and generally being overall less active are likely to be suffering one of several respiratory diseases. Reference movement pattern data modeling this movement pattern is stored as a definition in the physical condition table to allow animals exhibiting this movement pattern to be identified quickly. In this manner, early identification of animals suffering respiratory diseases can be achieved allowing animals to be treated in the hospital and processing area 22 quickly and returned to the feedlot 10.

It has also been determined that animals moving very little are likely to be suffering a muscular skeletal injury. Reference movement pattern data modeling this movement pattern is stored as a definition in the physical condition table to allow animals exhibiting this movement pattern to be identified quickly. In this manner, early identification of animals suffering muscular skeletal injuries can be achieved allowing animals to be treated quickly in the hospital and processing area 22 and returned to the feedlot 10. In addition, it has been determined that stationary animals or animals moving in a circle in one direction likely suffer neurological disorders. Reference movement pattern data modeling these movement patterns is stored as definitions in the physical condition table to allow animals exhibiting these movement patterns to be identified quickly. In this case, the animals can be shipped from the feedlot 10 early to reduce production costs.

It has also been determined that animals visiting the water zone often and for short durations or visiting the water zone infrequently and for short durations are likely to be suffering gastrointestinal disorders. Reference movement pattern data modeling these movement patterns is stored as definitions in the physical condition table to allow animals exhibiting these movement patterns to be identified quickly. Early detection of animals suffering gastrointestinal disorders can prevent animal death through treatment at the hospital and processing area 22.

Performance Characteristics

With respect to performance characteristics, it has been determined that yield grade and quality grade of cattle can be correlated to the frequency and duration cattle spend in the food zone of the feedlot pen 12. Referring now to FIG. 7a, a graph showing the frequency and duration cattle of different yield grades spend feeding over an eight week period is illustrated. As can be seen, cattle having a yield grade 1 consistently spend more time in the food zone and visit the food zone more often than cattle of other yield grades. Accordingly, cattle showing a pattern of higher frequency visits and longer duration visits in the food zone relative to other animals will have a better yield grade. Reference movement pattern data modeling the graphical data is stored as definitions in the physical condition table to allow animals to be classified according to yield grade and grouped if desired.

Figure 7B:
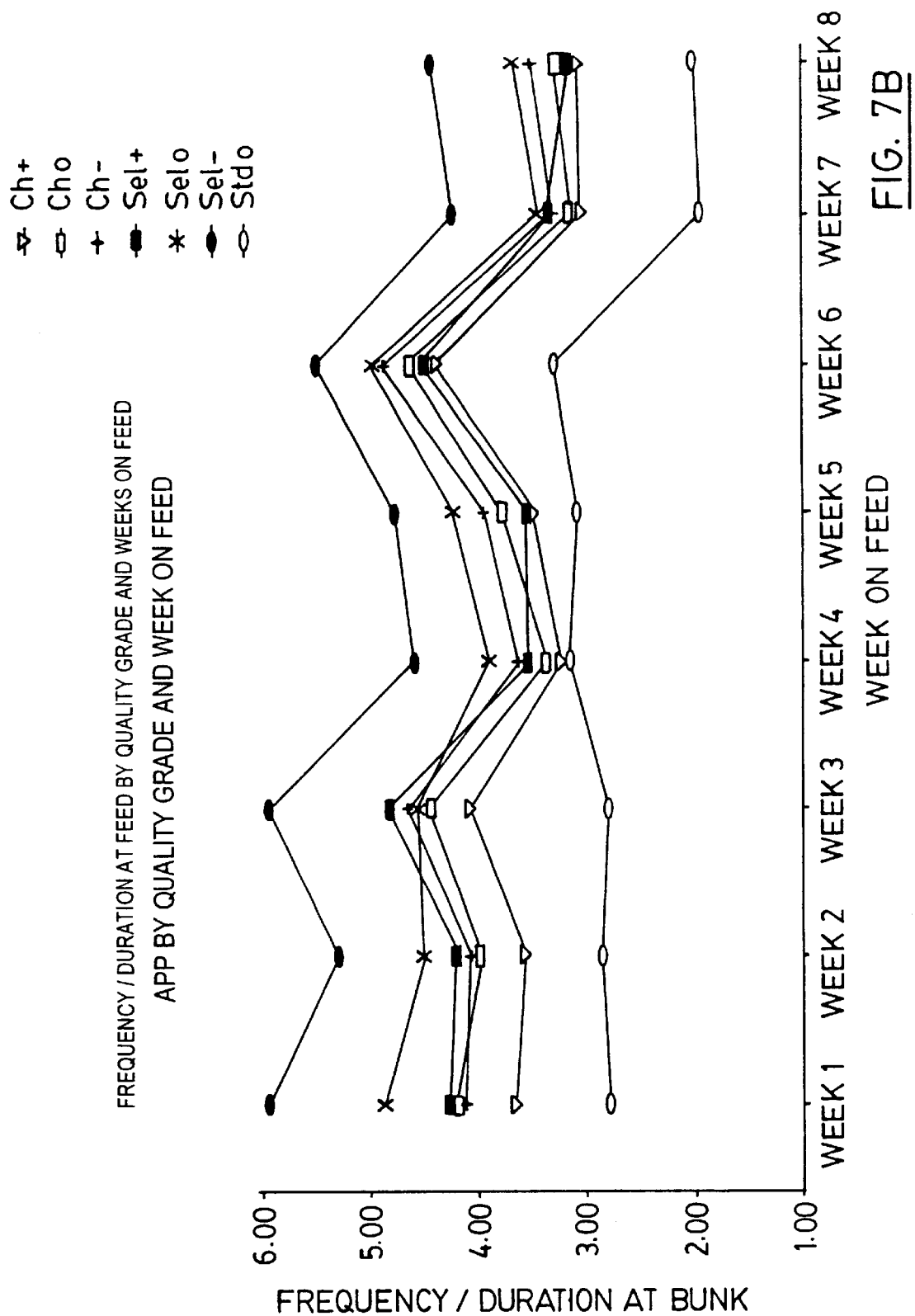

FIG. 7b shows a graph of the frequency and duration cattle of different quality grades spend in the food zone over an eight week period. As can be seen, cattle having a high quality grade consistently spend less time in the food zone and visit the food zone less often than cattle of other quality grades. Reference movement pattern data modeling the graphical data is stored as definitions in the physical condition table to allow animals to be classified according to quality grade and grouped if desired.

FIG. 7c shows a graph of the frequency and duration cattle having different amounts of back fat spend in the food zone over an eight week period. As can be seen, cattle having less back fat consistently spend more time in the food zone and visit the food zone more often than cattle having more back fat. This is important since the amount of back fat carried by the animal will effect its yield grade. Reference movement pattern data modeling the graphical data is stored as definitions in the physical condition table to allow animals to be classified according to back fat percentage and grouped if desired.

Figure 7D:
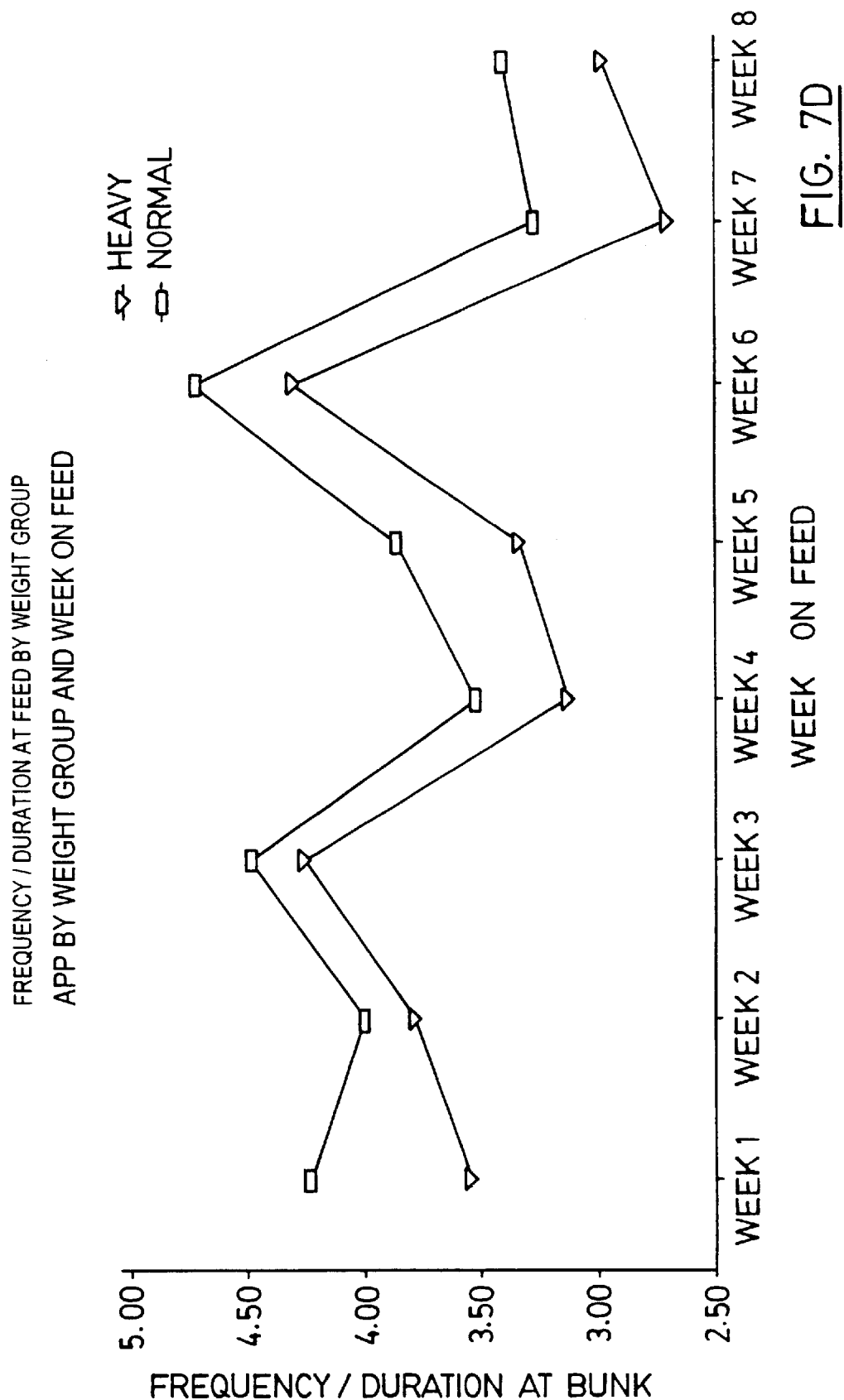

FIG. 7d shows a graph of the frequency and duration cattle of different weight groups spend in the food zone over an eight week period. As can be seen, cattle classified as "heavy" consistently spend less time in the food zone and visit the food zone less often than normal weight cattle. This is important since heavy animals are frequently discounted due to the fact that they are over fat and do not meet size and handling standards at slaughterhouses. Reference movement pattern data modeling the graphical data is stored as definitions in the physical condition table to allow animals to be classified according to weight and grouped if desired.

Production Patterns

With respect to production characteristics, animals spending less time in the food zone and visiting the food zone less nearing the end of their stay in the feedlot, can be identified as being market ready. This characteristic can be clearly seen in the graphs of FIGS. 7a and 7b. Reference movement pattern data modeling this movement pattern is stored as a definition in the physical condition table to allow animals showing this movement pattern to be identified quickly. Identified market ready animals can be shipped to the slaughterhouse timely. This maintains high performance standards in the feedlot by inhibiting animals from remaining in the feedlot too long. Animals remaining in the feedlot 10 while on feed too long tend to gain extra skeletal fat which of course reduces performance. In addition, lengthening the stay of animals in the feedlot while on feed increases greenhouse gas emissions.

Definitions including reference movement pattern data modeling animal movement patterns where most animals move to the food zone when the feed truck passes or when few animals move to the food zone when the feed truck passes are also stored in the physical definition table. In the former case, insufficient feeding of animals having high energy requirements can be detected quickly and their feed rations adjusted accordingly. In the later case, overfeeding of animals can be detected quickly and their feed rations adjusted accordingly, thereby to lower feed costs.

Referring now to FIG. 5b, some of the physical condition definitions are better illustrated. As can be seen, the reference movement pattern data includes threshold levels to which the movement patterns of the animals are compared. For example, in the case of the physical condition definition relating to respiratory disorders, the reference movement pattern data includes threshold levels to indicate high frequency and long duration visits to the water zone, low frequency and short duration visits to the food zone as well as overall general low activity. The physical condition definition relating to gastrointestinal disorders has reference movement pattern data including threshold levels to indicate high frequency and short duration visits to the water zone and low frequency and short visits to the food zone.

The physical condition definition relating to yield grade 1 at a specific stage determined by days on feed has reference movement pattern data including threshold levels to indicate high frequency and long duration visits to the food zone as well as days on feed. The physical condition definition relating to market ready animals has reference movement pattern data including threshold levels to indicate medium frequency and medium duration visits to the food zone as well as days on feed. Animal movement pattern data is compared with these threshold levels to determine if animals meet the definitions.

The operation of the present method and system for monitoring animals will now be described.

When animals arrive in the feedlot in preparation for slaughter, the animals proceed through the feedlot 10 in stages. Typically, animals proceed through the feedlot in three stages, namely an early stage, a growth stage and a finish stage. Table 1, shows the time, ration, health protocol and animal movement patterns of interest during each stage. To improve performance of the feedlot, it is desired to identify and treat sick animals quickly, to classify animals according to one or more performance characteristics so that feed composition and rations can be adjusted accordingly, and to monitor production patterns so that market ready animals and undesired feedlot conditions can be detected quickly. The method and system according to the present invention provides for the above.

Figures 1, 4, 5A:
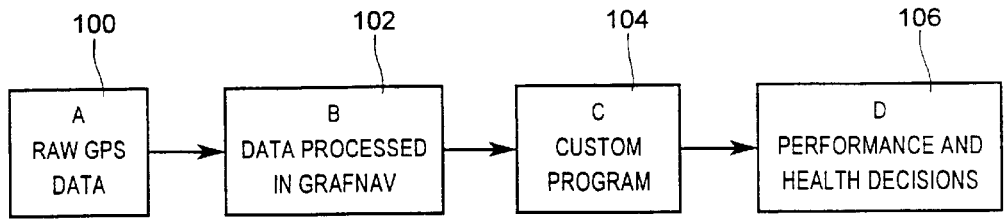

At selected intervals, in this case approximately every 15 seconds, the GPS receiver 34 in each data collection and transmission unit 32 is conditioned by the microcontroller 38 to poll the GPS satellites 33 and collect raw GPS data representing the associated animal's position within the feedlot pen 12 (see block 100 in FIG. 4). The raw GPS data is then conveyed to the microcontroller 38. When the high frequency and long duration visits to the water zone, low frequency and short duration visits to the food zone as well as overall general low activity. The physical condition definition relating to gastrointestinal disorders has reference movement pattern data including threshold levels to indicate high frequency and short duration visits to the water zone and low frequency and short visits to the food zone.

The physical condition definition relating to yield grade 1 at a specific stage determined by days on feed has reference movement pattern data including threshold levels to indicate high frequency and long duration visits to the food zone as well as days on feed. The physical condition definition relating to market ready animals has reference movement pattern data including threshold levels to indicate medium frequency and medium duration visits to the food zone as well as days on feed. Animal movement pattern data is compared with these threshold levels to determine if animals meet the definitions.

The operation of the present method and system for monitoring animals will now be described.

When animals arrive in the feedlot in preparation for slaughter, the animals proceed through the feedlot 10 in stages. Typically, animals proceed through the feedlot in three stages, namely an early stage, a growth stage and a finish stage. Table 1, shows the time, ration, health protocol and animal movement patterns of interest during each stage. To improve performance of the feedlot, it is desired to identify and treat sick animals quickly, to classify animals according to one or more performance characteristics so that feed composition and rations can be adjusted accordingly, and to monitor production patterns so that market ready animals and undesired feedlot conditions can be detected quickly. The method and system according to the present invention provides for the above.

At selected intervals, in this case approximately every 15 seconds, the GPS receiver 34 in each data collection and transmission unit 32 is conditioned by the microcontroller 38 to poll the GPS satellites 33 and collect raw GPS data representing the associated animal's position within the feedlot pen 12 (see block 100 in FIG. 4). The raw GPS data is then conveyed to the microcontroller 38. When the microcontroller 38 receives the raw GPS data, it stores the raw GPS data in its resident memory together with a time stamp.

The interrogator 50 is programmed to poll the data collection and transmission units 32 in a predetermined sequence to read the raw GPS data and time stamps stored therein at intervals. Specifically, the interrogator 50 continuously cycles through each data collection and transmission unit 32 in numerical order. If a data collection and transmission unit 32 cannot be read due to a lack of a clean line of sight, the interrogator 50 skips that data collocation and transmission unit 32 and attempts to read it during the next cycle.

When a data collection and transmission unit is being read by the interrogator 50, the interrogator 50 sends an addressed command to that data collection and transmission unit 32 by way of a wireless RF communications link. When the RFID engine 40 in the data collection and transmission unit 32 receives the command, the command is passed to the microcontroller 38. Upon receiving the command, the microcontroller 38 responds to the command by sending the raw GPS data and time stamp stored in its resident memory to the RFID engine 40. The RFID engine 40 in turn transmits the raw GPS data and time stamp together with an identifier to the interrogator 50 via the wireless RF communications link. When the interrogator 50 receives the transmitted data from the data collection and transmission unit 32, it conveys the data to the processor 52.

When the processor 52 receives the raw GPS data, time stamp and identifier from one of the data collection and transmission units 32, the received data is processed using GrafNav software by Waypoint Consulting to increase the accuracy of the GPS data and is placed as an entry into the animal observation table (block 102). The time stamp is synchronized to GPS time and is adjusted for local time. The animal observation table in the present embodiment is in the form of an SQL database. Each entry made in the SQL database takes the form:

("Tag Number", "X", "Y", "Time")

where:
"Tag Number" is the data collection and transmission unit identifier;
"X" and "Y" represent the animal position either in latitude and longitude or in co-ordinates referenced to a survey point; and
"Time" is the microcontroller time stamp.

Since the interrogator 50 continuously cycles through the data collection and transmission units 32, the SQL database is continuously updated at intervals to provide current and historical positional data concerning each of the animals in the feedlot pens 12. In this manner, a record of each animal's movement pattern within the feedlot pen 12 is maintained.

The processor 52 which communicates with the processor 54, downloads the SQL database to the processor 54 at predetermined intervals so that animal movement pattern data over a fixed time period is received by the processor 54. Once the SQL database has been downloaded, the processor 54 executes a routine and using the SQL database and the zone definition table creates a virtual table including the animal observation table entries together with current and previous zone position information (block 104). The entries in this virtual table take the form:

("Tag Number", "X", "Y", "Time", "Zone In", "Zone From")

where:
"Zone In" represents the current zone position of the animal; and
"Zone From" indicates whether the animal has moved from one zone to another between successive entries in the table.

FIG. 5c illustrates an example of the virtual table for a single animal identified as "A". As can be seen, the Zone In and Zone From entries indicate the general movement pattern of animal A in the feedlot pen 12 over a period of time. The X and Y coordinate data entries provide detailed movement pattern data concerning animal A over the same period of time.

Once this virtual table is created, the processor 54 executes another routing to compare the virtual table with the physical condition definitions to determine whether the animals exhibit any of the physical conditions of interest as defined by the reference movement pattern data. The reference movement pattern data function as benchmarks to which the animals under observation can be compared. By comparing the virtual table contents with the physical condition definitions, animal health and performance characteristics decisions can be made (block 106).

For example, when the virtual table of FIG. 5c is being compared with the respiratory disorder definition in the physical condition table, the processor 54 calculates:
the frequency animal A visited the water zone using the Zone In, Zone From and Time entries;
the duration animal A spent in the water zone using the Zone In and Time entries;
the frequency animal A visited the food zone using the Zone In, Zone From and Time entries;
the duration animal A spent in the food zone using the Zone In and Time entries; and the general overall activity of the animals using the X and Y coordinate data entries.

The calculated values are then compared with the threshold levels in the definition. If the animal meets all of the conditions, the animal is considered to be suffering a respiratory disorder.

The above process is performed in respect of the animal movement data for each of the animals in the feedlot and a comparison between the animal movement data and each of the definitions in the physical condition table is made. The results of the comparisons are displayed via the GUI allowing feedlot owners to identify sick animals, classify other animals according to performance characteristics and take measures to deal with identified production patterns. Animals identified as being sick are generally presented in a list according to disorder. With respect to animals classified according to performance characteristics, the animals can be presented in a list or alternatively the movement patterns of the animals can be presented graphically. With respect to animals classified according to performance characteristics, market ready animals are generally presented in a list, while overfeeding and underfeeding conditions are presented as display screens to the feedlot operator.

In addition to the above, since the movement patterns of the animals in the feedlot 10 are monitored, changes in the overall feeding patterns of the animals can be detected. It is known that the feeding patterns of the animals change at each stage in the feedlot as illustrated in Table 1. By detecting changes in feed patterns of animals quickly, operators can apply the appropriate protocols for specific animals at the appropriate time to optimize processing of the animals through the feedlot. This allows the feedlot operator to determine the proper time to implant hormones. This also allows an operator to control the composition and/or amount of feed supplied to the animals which has a three-fold beneficial effect. Firstly, by controlling the composition and/or amount of feed supplied to the animals, feed costs can be reduced. Secondly, in the case of high grade animals, feed can be controlled to inhibit the animals from gaining too much fat and weight which results in the penalties for over fat/over large cattle. Lastly, by reducing the number of days the animals are placed on feed and/or by customizing the animals' diet, the animals produce less methane thereby reducing production of greenhouse gases. Although reducing greenhouse gasses has an environmental benefit, another advantage exists. Greenhouse gas reductions can be sold as offsets to entities producing significant quantities of greenhouse gasses to allow these entities to meet greenhouse gas emission levels. This is achieved by determining the difference in time the market ready animals spent in the feedlot with the average industry time an animal spends in a feedlot and estimating the amount of methane gas the animals would have produced over that difference in time.

As one of skill in the art will appreciate, based on the results of animal movement patterns, sick animals can be quickly detected and treated for health problems. Animals showing other similar conditions can be detected and grouped and decisions can be made concerning the optimization of production. After animals under observation have been slaughtered, carcass data can be obtained from the packer and reviewed relative to the definitions to allow the definition reference movement pattern data to be updated. Once the reference movement pattern data has been updated, the current and historical animal movement pattern data can be reprocessed in the manner described above using the updated definitions thereby enhancing the accuracy of the present method and system.

Figure 6:
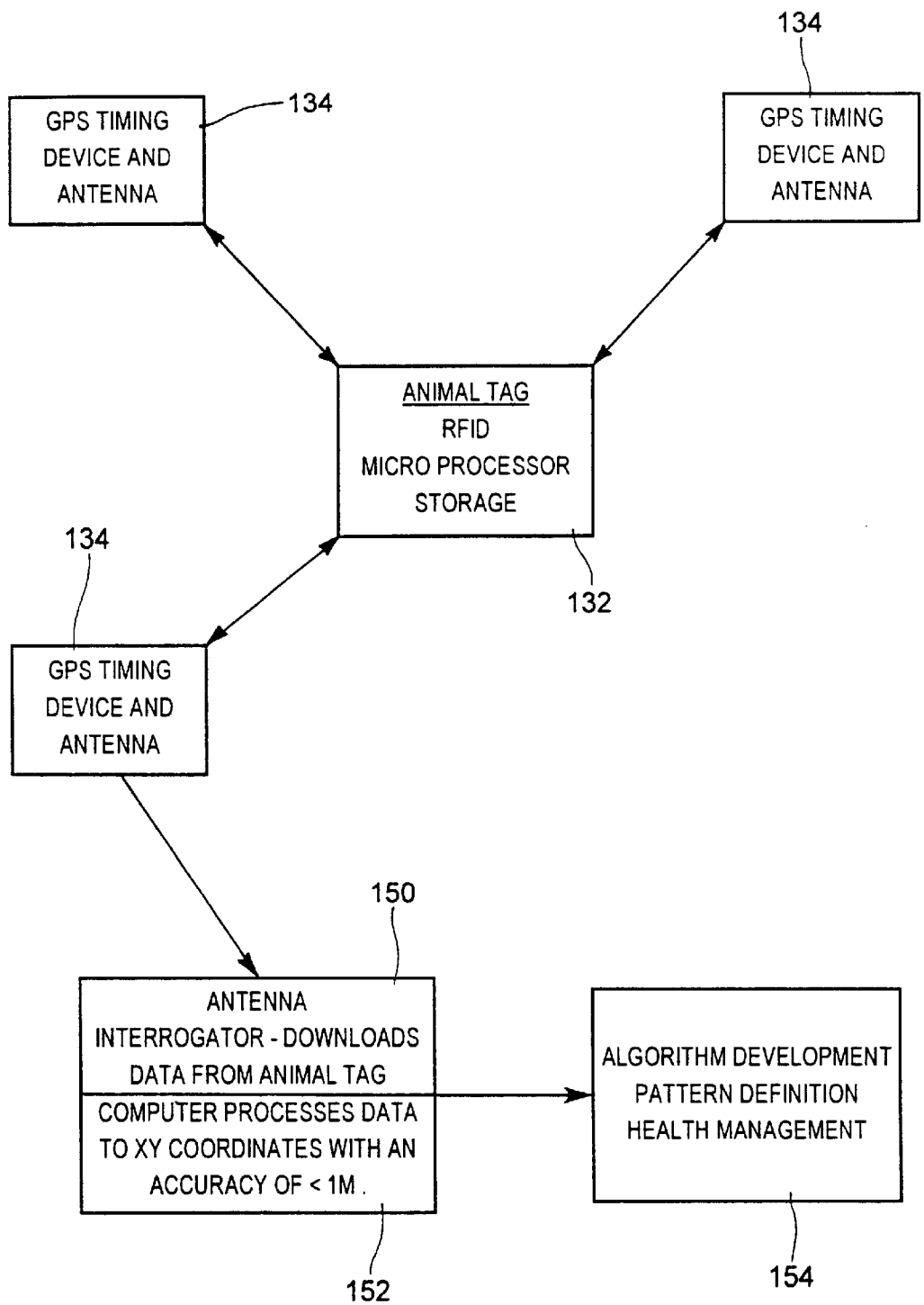
FIG. 6 is an alternative embodiment of a system for feedlot management in accordance with the present invention.

Although the system has been described as including data collection and transmission units communicating with GPS satellites to generate raw GPS data, those of skill in the art will appreciate that alternative methods for generating position data can be used. For example, as is shown in FIG. 6, three GPS timing devices 134 can be positioned at various locations in the feedlot 10 with each GPS timing device communicating with RFID animal tags 132 carried by the animals that include data collection and transmission units 32. In this case, raw GPS data is acquired by each GPS timing device. Each GPS timing device 134 in turn sends the raw GPS data to the data collection and transmission units on the RFID animal tags. The data collection and transmission unit in each RFID animal tag records the raw GPS data together with time stamps. When a data collection and transmission unit is polled by the interrogator 150, the data collection and transmission unit sends the raw GPS data and time stamps to the interrogator 150. The interrogator 150 in turn passes the information to the processor 152 which enhances the accuracy of the GPS data and then calculates the XY coordinates of the data collection and transmission unit 32 by triangulation. The data is then downloaded to the processor 154 and processed in the manner described previously.

Although the system and method of the present invention have been described specifically with reference to a feedlot environment, those of skill in the art will appreciate that the movement of animals can be monitored in other environments, such as for example in pastures or grazing pens. In this case, the movement of animals can be monitored to determine if the animals suffer from any of the above noted health problems. In addition to the above, definitions including reference movement pattern data modeling the typical movement patterns of animals exhibiting conditions of interest in this environment can be stored in the physical condition table (see Table 2). Typical movement patterns of interest in this environment include but are not limited to:

the movement of animals to a calving zone at inappropriate times indicating the likelihood of reproductive disorders;

the grouping of female animals indicating animals in heat;

the movement of animals along the perimeter of the grazing pen or pasture indicating low food levels; and the grouping of animals at the water zone for long durations indicating poor water quality.

In addition to the above, by monitoring the movement patterns of animals in the pasture or grazing pen, heavily used grazing areas can be determined allowing measures to be taken to increase feed in those areas or to move animals to other feeding areas.

The software executed by the processor 54 including the table of FIG. 5b can be downloaded to the processor from a remote location over a network link or can be shred on a physical medium such as a floppy disk or CD-ROM and then loaded onto the processor 54. This allows the software to be supplied to parties having their own animal tracking hardware.

Although particular embodiments of the present invention have been described, those of skill in the art will appreciate that variations and modifications may be made without departing from the spirit and scope thereof as defined by the appended claims.

TABLE 1

|  | Entry | Growth | Finish |
| --- | --- | --- | --- |
| Day | 1–43 | 43– about 100 | 100–180 |
| Ration | 1–6 | 7 | 8 |
| Health Protocol | Entry Protocol Treat individual sick animals. | Treat individual sick animals and do appropriate mass treatments | Monitor all animal treatments |
| Pattern Information | Vary rations to facilitate optimal progression through the orientation period. Monitor animal health as this is the highest risk period for sickness and morbidity. Patterns identifying respiratory and gastrointestinal disease are most important in this stage. | Identify poor health (patterns for respiratory, gastrointestinal, muscular, and neurological disease are important in this stage.) Identify like animals (through feeding/sleep/ eating and weight gain patterns) and then group for mass treatments. Identify animals with patterns indicating not gaining on ration. | Identify animals at optimal "finish point" (patterns of declining frequency in food zone) as feeding past this point has a very high cost of gain. Identify optimal yield and quality grade. Identify earliest endpoint to reduce greenhouse gas emissions. |

TABLE 2

|  | Diagnosis/Action | Benefit |
| --- | --- | --- |
| Health Patterns | | |
| Increased water consumption, decreased feed, decreased activity | High Rectal Temperature | Early identification of several respiratory diseases |
| High frequency, short duration water, low frequency, low duration at food zone. | Gastrointestinal illness | Early detection lowers morbidity |
| Low levels moving | Muscular skeletal injury | Early treatment |
| Not moving | Neurological disease | Early treatment or early shipping to reduce costs. |
| Animal circles in one direction | Neurological disease | Early treatment or early shipping to reduce costs. |
| Moving to calving zone | Reproductive disorder | Can pull animals and watch during this high risk process |
| Production Patterns | | |
| Lower and shorter visits to food zone in last month in feedlot | Animal is market ready | All animals kept past this optimal point have a higher extra skeletal fat level and have a lower yield grade. |
| Most animals move to food zone when feed truck passes | Insufficient feed | Early indentification of high energy requirements. |
| Few animals move to food zone when feed truck passes | Over feeding | Lower costs. |
| Animals grouping with long duration at water zone | Poor water quality | Early identification allows early correction in range situations. |
| Females grouping | Animals in heat | Higher pregnancy rates |
| Monitor grazing patterns | Identify heavy use areas | Effective use of grass and prevention of overgrazing |
| Animals walking the perimeter of the enclosure | Low food levels | Prevention of starvation |

We claim:

1. A method of monitoring the movement of animals within an area comprising the steps of:
   collecting positional data of each animal under observation;
   processing said positional data to generate movement pattern data representing the movement patterns of said animals; and
   analyzing said movement pattern data to determine at least one physical condition of said animals, wherein during said analyzing step said movement pattern data is compared with reference movement pattern data stored in a database that represents typical movement patterns of animals exhibiting said at least one physical condition.

2. The method of claim 1 wherein said positional data is collected remotely and at intervals.

3. The method of claim 1 wherein said movement pattern data is compared with said reference movement pattern data to detect animals suspected of suffering a health problem.

4. The method of claim 3 wherein said movement pattern data is compared with said reference movement pattern data to detect generally stationary animals thereby to determine animals suspected of suffering a muscular skeletal injury and/or a neurological disorder.

5. The method of claim 3 wherein said movement pattern data is compared with said reference movement pattern data to detect animals circling in one direction thereby to determine animals suspected of suffering a neurological disorder.

6. The method of claim 3 wherein said area is divided into at least two zones including a food zone and a water zone and wherein said movement pattern data is compared with said reference movement pattern data to detect the duration and frequency said animals spend in at least one of said zones thereby to determine animals exhibiting said at least one physical condition.

7. The method of claim 6 wherein said movement pattern data is compared with said reference movement pattern data to detect animals visiting said water zone more frequently and spending more time in said water zone at each visit thereby to determine animals suspected of suffering a respiratory disorder.

8. The method of claim 7 wherein said movement pattern data is further compared with said reference movement pattern data to detect animals exhibiting generally overall decreased movement within said area.

9. The method of claim 6 wherein said movement pattern data is compared with said reference movement pattern data to detect animals visiting said water zone more frequently and spending less time in said water zone at each visit thereby to determine animals suspected of suffering a gastrointestinal disorder.

10. The method of claim 6 wherein said movement pattern data is compared with said reference movement pattern data to detect animals visiting said water zone less frequently and spending less time in said water zone at each visit thereby to determine animals suspected of suffering a gastrointestinal disorder.

11. The method of claim 6 wherein said movement pattern data is compared with said reference movement pattern data to detect animals exhibiting one or more of the following movement characteristics:
   (i) more frequent and longer duration visits to said water zone;
   (ii) less frequent visits to said food zone;
   (iii) generally overall decreased movement within said area;
   (iv) more frequent and shorter duration visits to said water zone; and
   (v) less frequent and shorter duration visits to said water zone.

12. The method of claim 3 wherein said movement pattern data is compared with said reference movement pattern data to detect animals exhibiting one or both of the following characteristics:
   (i) generally little movement within said area; and
   (ii) circling in one direction.

13. The method of claim 12 further comprising the step of removing animals from said area which exhibit one or both of said characteristics.

14. The method of claim 1 wherein said area is divided into at least two zones, one of said zones being a food zone and wherein said movement pattern data is compared with said reference movement pattern data to detect movement of said animals relative to said food zone.

15. The method of claim 14 wherein said movement pattern data is compared with said reference movement pattern data to detect the frequency and duration animals spend in said food zone.

16. The method of claim 15 wherein said movement pattern data is compared with said reference movement pattern data to determine a yield grade for each animal.

17. The method of claim 16 wherein said movement pattern data is compared with reference movement pattern data representing animals of optimal, standard and minimum yield grades to allow said animals under observation to be classified into optimum, standard and minimum yield grades as a function of days on feed.

18. The method of claim 15 wherein said movement pattern data is compared with said reference movement pattern data to determine a quality grade for each animal.

19. The method of claim 15 wherein said movement pattern data is compared with said reference movement pattern data to determine a back fat percentage of each animal.

20. The method of claim 15 wherein said movement pattern data is compared with said reference movement pattern data to determine a weight group for each animal.

21. The method of claim 14 wherein said movement pattern data is compared with said reference movement pattern data to determine market ready animals.

22. The method of claim 21 further comprising the step of changing feeding patterns for market ready animals thereby to reduce greenhouse gas production.

23. The method of claim 22 further comprising the step of calculating reductions in greenhouse gas production and selling the greenhouse gas reductions as offsets to greenhouse gas producers.

24. A system for monitoring the movement of animals within an area including a food zone and a water zone comprising:
   a plurality of data collection and transmission units, each being carried by a respective animal, each of said data collection and transmission units transmitting animal position data over a wireless communications link; and
   a processor in communication with said data collection and transmission units via said wireless communication link and receiving said animal position data, said processor processing said animal position data to generate data representing movement patterns of said animals and analyzing said movement pattern data to determine at least one physical condition of said animals, wherein said processor includes a database storing reference movement pattern data that represents typical movement patterns of animals suffering health problems, said processor comparing said movement pattern data with said reference movement pattern data to detect animals exhibiting one or more of the following movement characteristics:
   (i) more frequent and longer duration visits to said water zone;
   (ii) less frequent visits to said food zone;
   (iii) generally overall decreased movement within said area;
   (iv) more frequent and shorter duration visits to said water zone; and
   (v) less frequent and shorter duration visits to said water zone.

25. A system as defined in claim 24 wherein said processor further compares said movement pattern data with said reference movement pattern data to detect animals exhibiting one or both of the following characteristics:
  (i) generally little movement within said area; and
  (ii) circling in one direction.

26. The method of claim 14 wherein said movement pattern data is compared with said reference movement pattern data to detect overfeeding and underfeeding conditions of said animals.

27. The method of claim 21 further comprising the steps of shipping market ready animals to slaughter and calculating reductions in greenhouse gas production for sale as offsets to greenhouse gas producers.

28. A system as defined in claim 24 wherein said movement pattern data is further compared with said reference movement pattern data to determine a yield grade for each animal as a function of days on feed.

29. A system as defined in claim 24 wherein said movement pattern data is further compared with said reference movement pattern data to determine a quality grade for each animal as a function of days on feed.

30. A system for monitoring the movement of animals within an area including at least two zones, one of which is a food zone, comprising:
  a plurality of data collection an d transmission units, each being carried by a respective animal, each of said data collection and transmission units transmitting animal position data over a wireless communication link; and
  a processor in communication with said data collection an d transmission units via said wireless communication link and receiving said animal position data, said processor processing said animal position data to generate movement pattern data representing movement patterns of said animals and analyzing said movement pattern data to determine at least one physical condition of said animals, wherein said processor includes a database storing reference movement pattern data that represents typical movement patterns of animals having at least one physical condition of interest, said processor comparing said movement pattern data with said reference movement pattern data to determine a yield grade for each animal as a function of days on feed.

31. A system for monitoring the movement of animals within an area including at least two zones, one of which is a food zone, comprising:
  a plurality of data collection and transmission units, each being carried by a respective animal, each of said data collection and transmission units transmitting animal position data over a wireless communication link; and
  a processor in communication with said data collection and transmission units via said wireless communication link and receiving said animal position data, said processor processing said animal position data to generate movement pattern data representing movement patterns of said animals and analyzing said movement pattern data to determine at least one physical condition of said animals, wherein said processor includes a database storing reference movement pattern data that represents typical movement patterns of animals having at least one physical condition of interest, said processor comparing said movement pattern data with said reference movement pattern data to determine a quality grade for each animal as a function of days on feed.

* * * * *